US008529947B2

(12) United States Patent
West et al.

(10) Patent No.: US 8,529,947 B2
(45) Date of Patent: Sep. 10, 2013

(54) ALKALOID FORMULATIONS (75) Inventors: Simon Michael West, Williamstown (AU); Esra Ogru, Glen Waverley (AU); Robert Gianello, Olinda (AU)

(73) Assignee: Vital Health Sciences Pty. Ltd., Melbourne (AU)

( * ) Notice: Subject to any disclaimer, the term of this patent is extended or adjusted under 35 U.S.C. 154(b) by 72 days.

(21) Appl. No.: 12/690,735

(22) Filed: Jan. 20, 2010

(65) Prior Publication Data

US 2010/0209459 A1 Aug. 19, 2010

Related U.S. Application Data (63) Continuation of application No. 10/551,203, filed as application No. PCT/AU2005/000307 on Mar. 3, 2005, now abandoned.

(30) Foreign Application Priority Data

Mar. 3, 2004 (AU) ................................ 2004901107
Aug. 3, 2004 (AU) ................................ 2004904367

(51) Int. Cl.
*A61K 9/20* (2006.01)
*A61K 9/00* (2006.01)

(52) U.S. Cl.
USPC .......................................... 424/464; 424/400

(58) Field of Classification Search
None
See application file for complete search history.

(56) References Cited

U.S. PATENT DOCUMENTS

| | | | |
|---|---|---|---|
| 2,407,823 A | 9/1946 | Fieser |
| 2,667,479 A | 1/1954 | Hoffman et al. |
| 2,913,477 A | 11/1959 | Hirschmann |
| 3,127,434 A | 3/1964 | Andrews |
| 3,212,901 A | 10/1965 | Robeson |
| 3,607,765 A | 9/1971 | Wixon |
| 4,075,333 A | 2/1978 | Josse |
| 4,141,938 A | 2/1979 | Klose |
| 4,299,906 A | 11/1981 | Liu |
| 4,369,172 A | 1/1983 | Schor et al. |
| 4,444,755 A | 4/1984 | Horrobin |
| 4,603,142 A | 7/1986 | Burger et al. |
| 4,654,373 A | 3/1987 | Bertelli |
| 4,684,520 A | 8/1987 | Bertelli |
| 4,686,211 A | 8/1987 | Hara et al. |
| 4,874,883 A | 10/1989 | Uphues et al. |
| 4,952,495 A | 8/1990 | Belly et al. |
| 4,977,282 A | 12/1990 | Baldwin et al. |
| 5,041,434 A | 8/1991 | Lubkin |
| 5,053,222 A | 10/1991 | Takasu et al. |
| 5,091,848 A | 2/1992 | Kojima |
| 5,094,848 A | 3/1992 | Brixner |
| 5,114,957 A | 5/1992 | Hendler et al. |
| 5,138,084 A | 8/1992 | Casagrande et al. |
| 5,173,304 A | 12/1992 | Lohner et al. |
| 5,334,378 A | 8/1994 | Mitani et al. |
| 5,374,645 A | 12/1994 | Kurihara-Bergstrom et al. |
| 5,387,579 A | 2/1995 | Meybeck et al. |
| 5,446,070 A | 8/1995 | Mantelle |
| 5,474,891 A | 12/1995 | Murphy |
| 5,474,991 A | 12/1995 | Ogata et al. |
| 5,554,781 A | 9/1996 | Reierson |
| 5,570,504 A | 11/1996 | Distefano et al. |
| 5,583,105 A | 12/1996 | Kovacs et al. |
| 5,589,504 A | 12/1996 | Dannenberg et al. |
| 5,603,949 A | 2/1997 | Meybeck et al. |
| 5,607,921 A | 3/1997 | Bernard et al. |
| 5,643,597 A | 7/1997 | Meybeck et al. |
| 5,656,618 A | 8/1997 | Meybeck et al. |
| 5,656,672 A | 8/1997 | Collin et al. |
| 5,741,518 A | 4/1998 | Ribier et al. |
| 5,759,526 A | 6/1998 | Simonnet et al. |
| 5,776,915 A | 7/1998 | Peterson et al. |
| 5,780,504 A | 7/1998 | Ptchelintsev |
| 5,804,168 A | 9/1998 | Murad |
| 5,804,216 A | 9/1998 | Terren et al. |
| 5,807,542 A | 9/1998 | Challis et al. |
| 5,807,845 A | 9/1998 | Ogata et al. |
| 5,885,595 A | 3/1999 | Corey et al. |
| 5,906,811 A | 5/1999 | Hersh |
| 5,908,846 A | 6/1999 | Bundgaard et al. |
| 5,916,915 A | 6/1999 | Eon et al. |
| 5,928,631 A | 7/1999 | Lucas et al. |
| 5,952,361 A | 9/1999 | Dias Nahoum |
| 5,952,373 A | 9/1999 | Lanzendorfer et al. |
| 5,965,750 A | 10/1999 | Oonishi et al. |
| 5,981,474 A | 11/1999 | Manning et al. |

(Continued)

FOREIGN PATENT DOCUMENTS

| | | |
|---|---|---|
| CA | 1337992 | 1/1996 |
| CA | 2426852 | 5/2002 |

(Continued)

OTHER PUBLICATIONS

United States Patent Office Action for U.S. Appl. No. 11/917,831 dated Jan. 19, 2011 (10 pages).
United States Patent Office Action for U.S. Appl. No. 12/628,443 dated Feb. 18, 2011 (15 pages).
Indian Patent Office Action for Application No. 2507/KOLNP/2006 dated Jan. 25, 2011 (1 page).
Schwenke, D.C. et al., "α-tocopherol protects against diet induced atherosclerosis in New Zealand white rabbits," J. Lipid Res. (2002) 43:1927-1938.
United States Patent Office Notice of Allowance for U.S. Appl. No. 10/485,196 dated Apr. 14, 2011 (7 pages).
United States Patent Office Action for U.S. Appl. No. 12/834,553 dated Apr. 14, 2011 (13 pages).
United States Patent Office Action for U.S. Appl. No. 11/817,453 dated Mar. 9, 2011 (12 pages).
Aberg, F. et al., "Distribution and redox state of ubiquinones in rat and human tissues," Arch. Biochem. Biophys. (1992) 295(2):230-234.
Almeida, M.E.M. et al., "Evaluation of soybean oil deodorization distillate for Vitamin E recovery," Arq. Biol. Tecnol. (1994) 37(4):1003-1011.
Barrett, C.W. et al., "The effect of particle size and vehicle on the percutaneous absorption of fluocinolone acetonide," Brit. J. Dermatol. (1965) 77:576-578.

(Continued)

*Primary Examiner* — Brian Gulledge
*Assistant Examiner* — Snigdha Maewall
(74) *Attorney, Agent, or Firm* — Michael Best & Friedrich LLP (57) ABSTRACT

There is provided an alkaloid formulation comprising the reaction product of one or more alkaloids with one or more phosphate derivatives of one or more electron transfer agents.

12 Claims, 6 Drawing Sheets

(56) References Cited

U.S. PATENT DOCUMENTS

| | | |
|---|---|---|
| 5,985,856 A | 11/1999 | Stella et al. |
| 6,022,867 A | 2/2000 | Ito et al. |
| 6,028,105 A | 2/2000 | Nigra |
| 6,046,181 A | 4/2000 | Oonishi et al. |
| 6,048,891 A | 4/2000 | Wechter |
| 6,096,326 A | 8/2000 | Wikholm |
| 6,121,249 A | 9/2000 | Weissman et al. |
| 6,143,770 A | 11/2000 | Lane et al. |
| 6,184,247 B1 | 2/2001 | Schneider |
| 6,231,885 B1 | 5/2001 | Carrara |
| 6,248,758 B1 | 6/2001 | Klokkers et al. |
| 6,248,779 B1 | 6/2001 | Shimizu et al. |
| 6,361,800 B1 | 3/2002 | Cooper et al. |
| 6,384,043 B1 | 5/2002 | Peyman et al. |
| 6,403,811 B1 | 6/2002 | West |
| 6,417,223 B1 | 7/2002 | Sanders et al. |
| 6,423,742 B1 | 7/2002 | Larson |
| 6,444,220 B2 | 9/2002 | Wiley |
| 6,444,234 B1 * | 9/2002 | Kirby et al. .................... 424/725 |
| 6,479,540 B1 | 11/2002 | Constantinides et al. |
| 6,485,950 B1 | 11/2002 | Kumar et al. |
| 6,503,545 B1 | 1/2003 | Perlman et al. |
| 6,579,995 B1 | 6/2003 | West |
| 6,599,933 B2 | 7/2003 | Takada et al. |
| 6,641,847 B1 | 11/2003 | Nawar |
| 6,645,998 B2 | 11/2003 | Sanders et al. |
| 6,703,384 B2 | 3/2004 | Sanders et al. |
| 6,727,280 B2 | 4/2004 | Palepu et al. |
| 6,770,672 B1 | 8/2004 | Sanders et al. |
| 6,887,648 B2 | 5/2005 | Pavelchek et al. |
| 7,074,825 B2 | 7/2006 | Mo et al. |
| 7,179,486 B1 | 2/2007 | Mulye |
| 2001/0006659 A1 | 7/2001 | Koike et al. |
| 2001/0044462 A1 | 11/2001 | Hensley et al. |
| 2002/0045765 A1 | 4/2002 | Kim et al. |
| 2002/0127198 A1 | 9/2002 | Rothbard et al. |
| 2002/0131994 A1 | 9/2002 | Schur et al. |
| 2002/0132845 A1 | 9/2002 | Miller et al. |
| 2002/0151467 A1 | 10/2002 | Leung |
| 2003/0035812 A1 | 2/2003 | Ito et al. |
| 2003/0109575 A1 | 6/2003 | Lambert et al. |
| 2003/0157326 A1 * | 8/2003 | Vaghefi et al. ............. 428/402.2 |
| 2003/0206972 A1 | 11/2003 | Babish et al. |
| 2003/0220301 A1 | 11/2003 | Lal et al. |
| 2004/0052754 A1 | 3/2004 | West et al. |
| 2004/0067890 A1 | 4/2004 | Gupta |
| 2004/0096493 A1 | 5/2004 | West |
| 2004/0097431 A1 | 5/2004 | Sanders et al. |
| 2004/0097472 A1 | 5/2004 | West et al. |
| 2004/0131569 A1 | 7/2004 | Schneider et al. |
| 2004/0167081 A1 | 8/2004 | Abbruzzese et al. |
| 2004/0204343 A1 | 10/2004 | Fishman |
| 2004/0234602 A1 * | 11/2004 | Fischer et al. ................. 424/473 |
| 2004/0235938 A1 | 11/2004 | Sanders et al. |
| 2004/0241225 A1 | 12/2004 | West |
| 2004/0253318 A1 | 12/2004 | West et al. |
| 2005/0009787 A1 | 1/2005 | West et al. |
| 2005/0089495 A1 | 4/2005 | West |
| 2005/0134664 A1 | 6/2005 | Pavlin |
| 2006/0120979 A1 | 6/2006 | Rubin |
| 2006/0228395 A1 | 10/2006 | Lamb et al. |
| 2006/0241085 A1 | 10/2006 | West et al. |
| 2006/0257459 A1 | 11/2006 | West et al. |
| 2006/0281715 A1 | 12/2006 | West |
| 2006/0281716 A1 | 12/2006 | West et al. |
| 2007/0042999 A1 | 2/2007 | West et al. |
| 2007/0135390 A1 | 6/2007 | West et al. |
| 2007/0141133 A1 | 6/2007 | Wang et al. |
| 2008/0233178 A1 | 9/2008 | Reidenberg et al. |
| 2008/0254073 A1 | 10/2008 | Chi |
| 2009/0004166 A1 | 1/2009 | West et al. |
| 2009/0005348 A1 | 1/2009 | Ogru et al. |
| 2009/0036354 A1 | 2/2009 | Gavin et al. |
| 2009/0104258 A1 | 4/2009 | Dumas et al. |
| 2009/0186856 A1 | 7/2009 | West et al. |
| 2009/0233881 A1 | 9/2009 | West et al. |
| 2009/0239827 A1 | 9/2009 | Ogru et al. |
| 2009/0274677 A1 | 11/2009 | Isaacs et al. |
| 2010/0076094 A1 | 3/2010 | West et al. |
| 2010/0222305 A1 | 9/2010 | West et al. |
| 2010/0261670 A1 | 10/2010 | West et al. |
| 2011/0003774 A1 | 1/2011 | West et al. |

FOREIGN PATENT DOCUMENTS

| | | |
|---|---|---|
| CA | 2426885 | 5/2002 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0612521 | 8/1994 |
| EP | 0617963 | 10/1994 |
| EP | 0641790 | 3/1995 |
| EP | 0643969 | 3/1995 |
| EP | 0661053 | 7/1995 |
| EP | 0669132 | 8/1995 |
| EP | 0669437 | 8/1995 |
| EP | 0674904 | 10/1995 |
| EP | 0679399 | 11/1995 |
| EP | 0680760 | 11/1995 |
| EP | 0681840 | 11/1995 |
| EP | 0684043 | 12/1995 |
| EP | 0699440 | 3/1996 |
| EP | 0826365 | 3/1998 |
| EP | 0845216 | 6/1998 |
| EP | 0699437 | 12/1998 |
| EP | 0965328 | 12/1999 |
| EP | 1000541 | 5/2000 |
| EP | 1023897 | 8/2000 |
| EP | 1053749 | 11/2000 |
| EP | 1264595 | 12/2002 |
| EP | 1470817 | 10/2004 |
| EP | 1783209 | 5/2007 |
| FR | 2777179 | 10/1999 |
| GB | 778142 | 7/1957 |
| GB | 1121683 | 7/1968 |
| GB | 2227662 | 8/1990 |
| JP | 50-022535 | 3/1975 |
| JP | 52-039013 | 3/1977 |
| JP | 53015381 | 2/1978 |
| JP | 58180410 | 10/1983 |
| JP | 59044375 | 3/1984 |
| JP | 59157091 | 9/1984 |
| JP | 60197621 | 10/1985 |
| JP | 61086940 | 5/1986 |
| JP | 61091137 | 5/1986 |
| JP | 61176535 | 8/1986 |
| JP | 61233631 | 10/1986 |
| JP | 62195393 | 8/1987 |
| JP | 63-093791 | 4/1988 |
| JP | 63139972 | 6/1988 |
| JP | 1228920 | 9/1989 |
| JP | 1274830 | 11/1989 |
| JP | 03-072426 | 3/1991 |
| JP | 03-120230 | 5/1991 |
| JP | 4208209 | 7/1992 |
| JP | 4270212 | 9/1992 |
| JP | 05-000946 | 1/1993 |
| JP | 5132700 | 5/1993 |
| JP | 5201858 | 8/1993 |
| JP | 5509296 | 12/1993 |
| JP | 6048962 | 2/1994 |
| JP | 6056699 | 3/1994 |
| JP | 6502422 | 3/1994 |
| JP | 6078214 | 10/1994 |
| JP | 6508820 | 10/1994 |
| JP | 7011291 | 1/1995 |
| JP | 7207298 | 8/1995 |
| JP | 7507318 | 8/1995 |
| JP | 7278587 | 10/1995 |
| JP | 7316170 | 12/1995 |

| | | |
|---|---|---|
| JP | 8073338 | 3/1996 |
| JP | 8193089 | 7/1996 |
| JP | 08-231564 | 9/1996 |
| JP | 8311085 | 11/1996 |
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 | 7/1999 |
| JP | 2000507557 | 6/2000 |
| JP | 2000198701 | 7/2000 |
| JP | 2001169731 | 6/2001 |
| JP | 2001247585 | 9/2001 |
| JP | 2002080475 | 3/2002 |
| JP | 2002088091 | 3/2002 |
| JP | 2003128531 | 5/2003 |
| JP | 2003171313 | 6/2003 |
| NZ | 244549 | 7/1994 |
| SU | 925961 | 5/1982 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 93/02661 | 2/1993 |
| WO | 93/09768 | 5/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | 96/37196 | 11/1996 |
| WO | WO 97/02803 | 1/1997 |
| WO | WO 97/14705 | 4/1997 |
| WO | WO 97/35591 | 10/1997 |
| WO | 99/35242 | 7/1999 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | WO 00/44237 | 8/2000 |
| WO | WO 00/44375 | 8/2000 |
| WO | 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | 00/74684 | 12/2000 |
| WO | WO 01/13901 | 3/2001 |
| WO | WO 01/19372 | 3/2001 |
| WO | WO 01/22937 | 4/2001 |
| WO | WO 01/35998 | 5/2001 |
| WO | WO 01/46204 | 6/2001 |
| WO | 01/54674 | 8/2001 |
| WO | WO 01/58889 | 8/2001 |
| WO | 01/072300 | 10/2001 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 02/40033 | 5/2002 |
| WO | WO 02/40034 | 5/2002 |
| WO | WO 03/011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 6/2003 |
| WO | WO 03/053407 | 7/2003 |
| WO | 03/068209 | 8/2003 |
| WO | 03/097714 | 11/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/084678 | 9/2005 |
| WO | WO 2006/012692 | 2/2006 |
| WO | WO 2006/092024 | 9/2006 |
| WO | WO 2006/092025 | 9/2006 |
| WO | WO 2006/133506 | 12/2006 |
| WO | WO 2007/070981 | 6/2007 |
| WO | 2008034178 | 3/2008 |
| WO | 2009146443 | 12/2009 |

OTHER PUBLICATIONS

Bikerman, J.J., "Mechanical destruction of young and old foam films," J. Phys. Chem. (1952) 56:164-165.

Blom, J.H. et al., "Reproductive success of female rainbow trout (Oncorhynchus mykiss) in response to graded dietary ascorbyl monophosphate levels," Biol. of Reproduction (1995) 52:1073-1080.

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.

De Wolfe, F.A. et al., "Ligand-binding proteins: their potential for application in systems for controlled delivery and uptake of ligands," Pharmacol. Rev. (2000) 52(2):207-236.

Devaraj, S. et al., "Modulation of monocyte-macrophage function with alpha-tocopherol: implications for atherosclerosis," Nat. Rev. (2002) 60(1):8-14.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Ernster, L. et al., "Biochemical, physiological and medical aspects of ubiquinone function," Biochim. Biophys. Acta (1995) 1271:195-204.

Fracalossi, D.M. et al., "Oscars, Astronotus ocellatus, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Gann, P.H. et al., "Lower prostate cancer risk in men with elevated plasma lycopene levels: results of a prospective analysis," Cancer Res. (1999) 59(6):1225-1230.

Gianello, R. et al., "α-tocopheryl phosphate: a novel, natural form of vitamin E," Free Radical Biol. Med. (2005) 39:970-976.

Godin, B. et al., "Ethosomes: new prospects in transdermal delivery," Crit. Rev. Thera. Drug Car. Syst. (2003) 20(1):63-102.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffin, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Heron-Milhavet, L. et al., "Muscle-specific overexpression of CD36 reverses the insulin resistance and diabetes of MKR mice," Endocrinology (2004) 145:4667-4676.

Imada, I. et al., "Photochemical Reaction of Ubiquinone. IV. Coenzymatic activity of ubiquinone and related compounds," Chem. Pharm. Bull. (1965) 13:136-142.

Iimura, N. et al., "Complex formation between cationic surfactantsand insoluble drugs," Bull. Chem. Soc. Jpn. (1999) 72:2417-2422.

Kagan, V. et al., "Antioxidant effects of ubiquinones in microsomes and mitochondria are mediated by tocopherol recycling," Biochem. Biophys. Res. Commun. (1990) 169(3):851-857.

Karrer, V.P. et al., "d,1-alpha-tocopherol-phosphorsaure-ester," Zurich, Chemisches Institut der Universitat (1933) p. 1137-1138, in German.

King, M.J. et al., "Transdermal delivery of insulin from a novel biphasic lipid system in diabetic rats," Diab. Tech. Therap. (2002) 4(4):479-488.

Knowler, W.C. et al., "Preventing Non-insulin-dependent diabetes," Diabetes (1995) 44:483-488.

Langsjoen, P.H. et al., "Overview of the use of CoQ10 in cardiovascular diseases," Biofactors (1999) 9:273-284.

Lass, A. et al., "Electron transport-linked ubiquinone-dependent recycling of α-tocopherol inhibits autooxidation of mitochondrial membranes," Arch. Biochem. Biophys. (1998) 352(2):229-236.

Lee, C-F. et al., "Attenuation of UV-induced apoptosis by coenzyme Q10 in human cells harboring large-scale deltion of mitochontrial DNA," Ann. N.Y. Acad. Sci. (2005) 1042:429-438.

Lei, B. et al.,. Progress in alpha-tocopherol preparation technology, Xiandai Huagong (1997) 17(7):13-15.

Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.

Mellors, A. et al., "The inhibition of mitochondrial peroxidation by ubiquinone and ubiquinol," J. Biol. Chem. (1966) 241(19):4353-4356.

Merck Index, The, "α-estradiol" Thirteenth Edition, Whitehouse Station, NJ (2001) p. 660.

Merck Index, The, "Fludarabine to Fludeoxyglucose F18" pages, Thirteenth Edition, Whitehouse Station, NJ (2001) pp. 729-730.

Min, J. et al., "Effect of apoptosis induced by different vitamin E homologous analogues in human hepatoma cells (HepG2)," J. Hygiene Res. China (2003) 32(4):343-345.

Miyamoto, S. et al., "Synthesis of a novel phosphate ester of a vitamin E derivative and its antioxidative activity," Biosci. Biotech. Biochem. (1998) 62(12):2463-2466.

Morgan, T.M. et al., "Transdermal delivery of estradiol in postmenopausal women with a novel topical aerosol," J. Pharm. Sci. (1998) 87(10):1226-1228.

Morgan, T.M. et al., "Enhanced transdermal delivery of sex hormones in swine with a novel topical aerosol," J. Pharm. Sci. (1998) 87(10):1219-1225.

Mortensen, S.A., "Perspectives on therapy of cardiovascular diseases with coenzyme Q10 (ubiquinone)," Clin. Investig. (1993) 71(Suppl. 8):S116-S123.

Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.

Negis, Y. et al., "On the existence of cellular tocopheryl phosphate, its synthesis, degradation and cellular roles: a hypothesis," IUBMB Life (2005) 57(1):23-25.

Octoplus, "Formulation Development of Poorly Soluble Drugs" (www.octoplus.n1) (1999) 2 pages (downloaded Nov. 2008).

Ogru, E. et al., "Vitamin E phosphate: an endogenous form of vitamin E," Medimond S.r.1. (2003) 127-132.

Ostrenga, J. et al., "Significance of vehicle composition I: Relationship between topical vehicle composition, skin penetrability, and clinical efficacy," J. Pharm. Sci. (1971) 60(8):1175-1179.

Owens, D.R. et al., "Alternative routes of insulin delivery," Diabet. Med. (2003) 20:886-898.

Parker et al., "Neonatal vitamin K administration and childhood cancer in the North of England: retrospective case-control study," BMJ (1998) 316:189-193.

Potts, R.O. et al., "Predicting skin permeability," Pharm. Res. (1992) 9(5):663-669.

Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.

Sevast'ianov, V.I. et al., "Transdermal delivery of insulin," Meditsinskaia Tekhnika (2003) 2:21-24.

Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.

Singh, R.B. et al., "Randomized double-blind placebo-controlled trial of coenzyme Q10 in patients with acute myocardial infarction," Cardiov. Drugs Ther. (1998) 12:347-353.

Stedman's Medical Dictionary, "Tocopherol," "Tocotrienol," and "Vitamin K1", 22nd Edition, Williams & Wilkins Co. (1972) p. 1303 and 1400.

Traber, M.G. et al., "Human plasma vitamin E kinetics demonstrates rapid recycling of plasma RRR-alpha-tocophero," Proc. Natl. Acad. Sci. USA (1994) 91:10005-10008.

Visarius, T. et al., "Inhibition of human prostate cancer cell proliferation: vitamin E and lycopene targeted pathways regulating cell cycle progression," FASEB J. (2004) 18(8):C103.

Younis et al., "The prevention of type 2 diabetes mellitus: recent advances," Q.J. Med. (2004) 97:451-455.

United States Office Action for U.S. Appl. No. 09/979,436 dated Apr. 4, 2002 (6 pages).

United States Office Action for U.S. Appl. No. 09/979,436 dated Sep. 23, 2002 (6 pages).

United States Office Action for U.S. Appl. No. 10/416,775 dated Nov. 2, 2005 (10 pages).

United States Office Action for U.S. Appl. No. 10/416,775 dated Jun. 12, 2006 (10 pages).

United States Office Action for U.S. Appl. No. 10/416,775 dated Jul. 12, 2007 (11 pages).

United States Office Action for U.S. Appl. No. 10/416,775 dated Dec. 17, 2008 (6 pages).

United States Office Action for U.S. Appl. No. 10/416,774 dated Sep. 6, 2007 (9 pages).

United States Office Action for U.S. Appl. No. 10/416,774 dated Jun. 11, 2008 (15 pages).

United States Office Action for U.S. Appl. No. 10/416,774 dated Feb. 17, 2009 (15 pages).

United States Office Action for U.S. Appl. No. 10/416,774 dated Apr. 15, 2009 (14 pages).

United States Office Action for U.S. Appl. No. 10/462,480 dated Dec. 1, 2006 (10 pages).

United States Office Action for U.S. Appl. No. 10/462,480 dated Nov. 1, 2007 (10 pages).

United States Office Action for U.S. Appl. No. 10/462,480 dated Feb. 20, 2009 (17 pages).

United States Patent Office Action for U.S. Appl. No. 10/462,480 dated Nov. 27, 2009 (9 pages).

United States Office Action for U.S. Appl. No. 10/485,196 dated May 29, 2008 (23 pages).

United States Office Action for U.S. Appl. No. 10/485,196 dated Jul. 23, 2009 (9 pages).

United States Office Action for U.S. Appl. No. 10/486,142 dated Mar. 18, 2008 (12 pages).

United States Office Action for U.S. Appl. No. 10/487,743 dated Dec. 2, 2005 (22 pages).

United States Office Action for U.S. Appl. No. 10/487,743 dated Jul. 27, 2006 (23 pages).

United States Office Action for U.S. Appl. No. 10/498,684 dated Oct. 2, 2008 (21 pages).

United States Office Action for U.S. Appl. No. 10/498,684 dated Jun. 23, 2009 (19 pages).

United States Office Action for U.S. Appl. No. 10/524,090 dated Mar. 12, 2008 (12 pages).

United States Office Action for U.S. Appl. No. 10/542,511 dated Aug. 8, 2007 (19 pages).

United States Office Action for U.S. Appl. No. 10/542,511 dated Mar. 31, 2008 (20 pages).

United States Office Action for U.S. Appl. No. 10/542,511 dated Feb. 5, 2009 (23 pages).

United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 11/817,453 dated Oct. 9, 2009 (11 pages).
Gianello, R. et al., "Subchronic oral toxicity study of mixed tocopheryl phosphates in rats," Int'l J. Toxicol. (2007) 26:475-490.
Libinaki, R. et al., "Evaluation of the safety of mixed tocopheryl phosphates (MTP)-a formulation of alpha-tocopheryl phosphate plus alpha-di-tocopheryl phosphate," Food Chem. Toxicol. (2006) 44(7):916-932.
Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.
Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.
Nakayama, S. et al., "Protective effects of a stable, water-soluble vitamin E on photodamage induced by UVB irradiation in cultured mouse skin," Photomedicine and Photobiology (1998) 20:99-100.
Negis, Y. et al., "Molecular mechanism of alpha-tocopheryl-phospate transport across the cell membrane," Biochem. Biophys. Res. Comm. (2007) 359:348-353.
Negis, Y. et al., "The effect of tocopheryl phosphates on atherosclerosis progression in rabbits fed with a high cholesterol diet," Arch. Biochem. Biophys. (2006) 450:63-66.
Rerek, M.E. et al., "Disodium lauriminodipropionate tocopheryl phosphates: a potent new anti-inflammatory," Cosmetics & Toiletries magazine (2003) 118(7):63-67.
Rezk, B.M. et al., "The extraordinary antioxidant activity of vitamin E phosphate," Biochim. Biophys. Acta (2004) 1683:16-21.
Suzuki, T. et al., "The solution behavior and the association structure of long-chain monoalkyl phosphates," Chem. Soc. Japan (1986) 633-640, with English abstract.
United States Patent Office Action for U.S. Appl. No. 10/416,774 dated Dec. 18, 2009 (11 pages).
United States Patent Office Action for U.S. Appl. No. 10/485,196 dated Jan. 25, 2010 (8 pages).
United States Patent Office Action for U.S. Appl. No. 12/212,803 dated Mar. 12, 2010 (13 pages).
United States Patent Office Action for U.S. Appl. No. 10/524,090 dated Mar. 3, 2010 (18 pages).
United States Patent Office Action for U.S. Appl. No. 10/542,511 dated Jan. 12, 2010 (13 pages).
United States Patent Office Advisory Action for U.S. Appl. No. 10/542,511 dated May 25, 2010 (3 pages).
United States Patent Office Action for U.S. Appl. No. 11/817,439 dated May 11, 2011 (11 pages).
United States Patent Office Action for U.S. Appl. No. 10/498,684 dated Jul. 7, 2010 (21 pages).
United States Patent Office Action for U.S. Appl. No. 11/817,453 dated Aug. 2, 2010 (10 pages).
United States Patent Office Action for U.S. Appl. No. 12/158,932 dated Aug. 19, 2010 (15 pages).
United States Patent Office Action for U.S. Appl. No. 12/628,443 dated Aug. 5, 2011 (8 pages).
United States Patent Office Action for U.S. Appl. No. 11/817,439 dated Jul. 29, 2011 (2 pages).
Walters et al., "The effects of surfactants on penetration across the skin" International Journal of Cosmetic Science (1993), vol. 15, pp. 260-270.

Devaraj, S. et al., "Alpha tocopherol decreases CD36 expression in human monocyte-derived macrophages," J. Lipid Res. (2001) 42:521-527.
Ricciarelli, R. et al., "Vitamin E reduces the uptake of oxidized LDL by inhibiting CD36 scavenger receptor expression in cultured aortic smooth muscle cells," Circulation (2000) 102:82-87.
Teupser, D. et al., "Alpha-tocopherol down-regulates scavenger receptor activity in macrophages," Atherosclerosis (1999) 144:109-115.
United States Patent Office Action for U.S. Appl. No. 10/485,196 dated Oct. 29, 2010 (13 pages).
Brandt, M., "Steroid hormone biosynthesis," (2002) printed from http://www.rose_hulman.edu/~brandt/Chem430/Steroids.pdf on Nov. 20, 2010 (7 pages).
Jiang, Q. et al., "γ-tocopherol, the major form of vitamin E in the U.S. diet, deserves more attention," Am. J. Clin. Nutri. (2001) 74(6):714-722.
United States Patent Office Action for U.S. Appl. No. 10/524,090 dated Nov. 23, 2010 (19 pages).
United States Patent Office Action for U.S. Appl. No. 11/817,439 dated Nov. 24, 2010 (15 pages).
United States Patent Office Action for U.S. Appl. No. 12/768,307 dated Oct. 6, 2011 (13 pages).
United States Patent Office Action for U.S. Appl. No. 12/782,564 dated Sep. 1, 2011 (10 pages).
United States Patent Office Action for U.S. Appl. No. 12/834,553 dated Oct. 7, 2011 (11 pages).
United States Patent Office Action for U.S. Appl. No. 11/817,453 dated Oct. 13, 2011 (14 pages).
United States Patent Office Action for U.S. Appl. No. 11/917,831 dated Oct. 24, 2011 (11 pages).
United States Patent Office Action for U.S. Appl. No. 12/782,560 dated Sep. 1, 2011 (18 pages).
Blum, A. et al., "Clinical and inflammatory effects of dietary L-arginine in patients with intractable angina pectoris," Amer. J. Cardiol. (1999) 1488-1489.
Isoda, K. et al., "Metformin inhibits proinflammatory responses and nuclear factor-κB in human vascular wall cells," Arterioscler. Thromb. Vasc. Biol. (2006) 26:611-617.
United States Patent Office Action for U.S. Appl. No. 11/572,864 dated Mar. 15, 2012 (15 pages).
Anslyn, E.V. et al., Modern Physical Organic Chemistry. Chapter 3: Solutiosn and Non-Covalent Binding Forces. University Science Books. (2006) see p. 146.
Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.
International Specialty Products,"A Product Guide. Performance enhancing Products for Pharmaceuticals," (2005) 20 pages [retrieved on Jul. 27, 2010 from http://web.archieve.org/web/20060623233652/http://abstracts.aapspharmaceutica. com/ExpoAAPS06/Data/EC/Event/Exhibitors/309/4ecb9a3a-65d0-4c69-a762-c60e099922ee.pdf, published on Jun. 23, 2006 as per Wayback Machine].
Mottu, F. et al., "Organic solvents for pharmaceutical parenterals and embolic liquids: a review of toxicity data," PDA Journal of Pharm. Sci. Tech. (2000) 54(6):456-469.
Williams, A.C. et al., "Penetration enhancers," Advanced Drug Delivery Reviews (2004) 56(5):603-618.
United States Patent Office Notice of Allowance for U.S. Appl. No. 12/628,443 dated Jan. 12, 2012 (7 pages).
Guthrie et al., VIIth Asian Conference of Nutrition: Lipid Symposium Proceedings, Journal of Nutrition, 1997, vol. 127, pp. 544s-548s.
Jiang, Q. et al., γ-tocopherol induces apoptosis in androgen-responsive LNCaP prostate cancer cells via caspase-dependent and independent mechanisms, Annals of the New York Academy of Sciences, 2004, vol. 103, pp. 399-400.
Koh, "Antioxidants in a carotenoid-rich edible oil," Journal of Japan Mibyou System Association, 2003, vol. 9, No. 1, pp. 12-13.

Pastori et al., "Lycopene in association with α-tocopherol inhibits at physiological concentrations proliferation of prostate carcinoma cells," Biochemical and Biophysical Research Communications, 1998, vol. 250, pp. 582-585.

United States Patent Office Action for U.S. Appl. No. 13/501,494 dated Dec. 18, 2012 (13 pages).

United States Patent Office Action for U.S. Appl. No. 13/501,500 dated Dec. 17, 2012 (14 pages).

Sinha, V.R. et al., "Coating polymers for colon specific drug delivery: A comparative in vitro evaluation," Ada. Pharm., 2003, vol. 53, pp. 41-47.

United States Patent Office Action for U.S. Appl. No. 12/782,438 dated Aug. 30, 2012 (14 pages).

United States Patent Office Action for U.S. Appl. No. 11/572,864 dated Nov. 8, 2012 (16 pages).

United States Patent Office Action for U.S. Appl. No. 11/817,439 dated Nov. 7, 2012 (10 pages).

Sharma H. et al., "An excerpt from the medical textbook Contemporary Ayurverda," Edinburgh: Churchill Livingston, 1998, 6 pages, Retrieved from Internet on Nov. 1, 2012 <URL: http://www.bsherman.net/freeradicals.htm>.

United States Patent Office Action for U.S. Appl. No. 13/577,124 dated Feb. 14, 2013 (15 pages).

United States Patent Office Action for U.S. Appl. No. 13/501,498 dated Feb. 21, 2013 (12 pages).

Maugard et al., "Synthesis of Water-Soluble Retinol Derivatives by Enzymatic Method," Biotechnol. Prog., 2002, vol. 18, pp. 424-428.

United States Patent Office Action for U.S. Appl. No. 13/683,698 dated Apr. 24, 2013 (18 pages).

\* cited by examiner

ALKALOID FORMULATIONS

CROSS-REFERENCE TO RELATED APPLICATIONS

This application is a continuation of U.S. patent application Ser. No. 10/551,203, filed Jun. 29, 2006, which is a national stage filing under 35 U.S.C. 371 of International Application No. PCT/AU2005/000307, filed Mar. 3, 2005, which claims priority to Australian Application No. 2004901107, filed Mar. 3, 2004 now abandoned, and Australian Application No. 2004904367, filed Aug. 3, 2004, the disclosures of each of which are incorporated by reference herein in their entireties. Priority to each application is hereby claimed.

FIELD OF THE INVENTION

The present invention is directed to formulations comprising one or more alkaloids. More specifically but not exclusively it relates to formulations comprising one or more alkaloids and one or more phosphate derivatives of electron transfer agents.

BACKGROUND OF THE INVENTION

In this specification, where a document, act or item of knowledge is referred to or discussed, this reference or discussion is not an admission that the document, act or item of knowledge or any combination thereof was at the priority date: part of common general knowledge, or known to be relevant to an attempt to solve any problem with which this specification is concerned.
Alkaloids There is a long history of the use of alkaloids for medicine. These compounds were originally extracted from plants and include nitrogenous compounds having physiological actions on humans as drugs and poisons. The term "alkaloids" as used in this description and in the claims includes all natural and synthetic active compounds containing primary, secondary or tertiary amine substituents. The amine may be incorporated into one or two rings, but non-cyclic structures are also included. For example, this includes:—
tertiary amines which:—
are alicyclic with the nitrogen atom as a common member of three rings (eg. Morphine, Atropine, Quinine); or
are cyclic where the nitrogen is incorporated into a single ring and alkylated (eg. Nicotine, Fenspiride); or
have no cyclic structure incorporating the nitrogen (eg. Flurazepan);
secondary amines where the nitrogen is incorporated into an alicyclic structure (eg Conline, Fendiline) or a linear structure (eg. Epinephrine);
primary amines (eg. Ephidrine);
pyridines (eg Nicotine);
methamidine derivatives;
quinolines (eg. Cinchonine); and
guanidines (eg. Arginine).

Most alkaloids are not water soluble but are soluble in organic solvents. However, all alkaloids are basic and will combine with acids to form crystalline salts which are usually at least partially water soluble. Typically, alkaloids are administered as salts either orally or by intravenous injection. The alkaloids are a class of drugs that are not commonly administered transdermally because the hydrophilic nature of the salts usually limits transdermal transport. Morphine and atropine are examples of clinically useful alkaloids that are not administered transdermally. Further, it is desirable to improve oral delivery of alkaloids since some of them are thought to act through the lymphatic system.

Topical Administration

Topical administration refers to the application of a drug directly to a part of the body and includes transdermal administration (application to the skin) and buccal administration (application to the inside of the mouth).

The skin is the largest organ of the body and functions to protect the internal organs from external chemical, physical and pathological hazards. Normal skin is divided into three layers: the epidermis, the dermis, and subcutaneous tissue. The outer cornified layer of the epidermis, the stratum corneum, possesses properties of strength, flexibility, high electrical impedance and dryness that retards penetration and proliferation of micro-organisms. The stratum corneum is also the principle barrier to transdermal drug absorption.

The art of transdermal delivery includes the application of drugs in the pure state or as formulations which typically include substances that enhance the rate of transport through the skin. Historically transdermal delivery was as ointments, creams, poultices and plasters to give effective contact with the skin. More recently, the technology has been improved by making the plaster into a "patch" which has better adhesion to the skin and improved control over the rate of transport.

Transdermal delivery has been recognized to offer several potential benefits including achieving blood levels similar to those achieved by slow intravenous infusion but without the inconvenience; better control of absorption and metabolism compared to oral administration; continuity of drug effect especially of drugs with short half lives; equivalent efficacy with reduced drug dosage due to by-pass of hepatic first pass elimination; lower risk of under or overdosing; and better patient compliance through simplification of a dosage regime.

Not every drug can be administered transdermally at a rate sufficiently high enough to achieve blood levels that are therapeutically beneficial for systemic medication. Drugs with similar molecular weights and sizes for example may absorb across the skin at different rates. Skin enhancers and various formulation techniques have been developed to improve drug absorption through the skin. But concern has been raised with respect to long term risk because increased drug permeability is achieved at the cost of damaging a fundamentally important protective layer of the skin.

Current strategies to improve transdermal therapy have not been universally successful and there is scope for further improvement. In particular, there is a need for use of transdermal delivery systems capable of delivering alkaloids.

There has also been increased interest in buccal delivery since this method of delivery avoids metabolism by the liver which can be a problem when drugs are administered orally. Typically, the drug is formulated in a lozenge which is placed under the tongue. The lining of the mouth does not have an equivalent of the stratum corneum on the skin so it is not as difficult to administer drugs by buccal delivery, but this method of administration is not commonly used because the rate of transport may be low, achieving an ineffective result if the buccal membranes do not allow permeation or active transport. Efforts have been made in the past to improve the topical administration of drugs. For example, international patent application no PCT/AU03/00998 discloses a carrier for pharmaceuticals wherein the carrier comprises a complex of a phosphate derivative of a pharmaceutically acceptable compound, for example, laurylaminodipropionic acid tocopheryl phosphates. PCT/AU03/00998 discloses that the tocopheryl phosphate is complexed to a complexing agent selected from the group consisting of amphoteric surfactants, cationic surfactants, amino acids having nitrogen functional groups and proteins rich in these amino acids. This carrier has been shown to improve the topical administration of testosterone, estrogen, atropine and morphine. However, in relation to morphine and atropine, further improvement in skin penetration was desired.

Oral Administration

Many drugs are administered orally, but a large number of potentially useful drugs are rejected because they are unable to pass through the intestinal walls. It is understood that substances such as fats are efficiently transported through the intestines, but many others such as tocopherol are poorly transported. There is thus a need for systems which enable improved oral administration of alkaloids.

SUMMARY OF THE INVENTION

It has been found that there is a significant improvement in administration when an alkaloid compound is complexed directly to a phosphate derivative of an electron transfer agent. For example, the administration of morphine was improved when it was complexed directly to tocopheryl phosphate.

According to the present invention, there is provided an alkaloid formulation comprising the reaction product of one or more alkaloids with one or more phosphate derivatives of one or more electron transfer agents.

Preferably, the phosphate derivative of a electron transfer agent is selected from the group comprising one or more phosphate derivatives of tocopherol.

Preferably, the alkaloid formulation is administered topically or orally.

According to a second aspect of the invention, there is provided a method for improving the efficacy of an alkaloid, said method comprising the step of reacting the alkaloid with one or more phosphate derivative of one or more electron transfer agents.

The present invention also provides for the use of the reaction product of one or more alkaloids with one or more phosphate derivatives of one or more electron transfer agents, together with excipients in the manufacture of a formulation.

The present invention also provides a pharmaceutical composition comprising the reaction product of one or more alkaloids with one or more phosphate derivatives of one or more electron transfer agents, such as phosphate derivatives of tocopherol.

Preferably, the alkaloid is selected from the group consisting of tertiary amines which are (1) alicyclic with the nitrogen atom as a common member of three rings (eg. Morphine, Atropine, Quinine); (2) are cyclic where the nitrogen is incorporated into a single ring and alkylated (eg. Nicotine, Fenspiride); or (3) have no cyclic structure incorporating the nitrogen (eg. Flurazepan). More preferably, the alkaloid is selected from the group consisting of atropine, quinine, opioids such as morphine, fentanyl, nicotine, fenspiride, flurazepan and codeine.

The term "electron transfer agents" is used herein to refer to the class of chemicals which may be phosphorylated and which (in the non-phosphorylated form) can accept an electron to generate a relatively stable molecular radical or accept two electrons to allow the compound to participate in a reversible redox system. Examples of classes of electron transfer agent compounds that may be phosphorylated include hydroxy chromans including alpha, beta, gamma and delta tocols in enantiomeric and racemic forms; quinols being the reduced forms of vitamin K1 and ubiquinone; hydroxy carotenoids including retinol; calciferol and ascorbic acid. Preferably, the electron transfer agent is selected from the group consisting of tocopherol and other tocols, retinol, vitamin K1 and mixtures thereof. More preferably, the electron transfer agent is selected from the group consisting of the tocols and mixtures thereof. The tocols include all isomers of derivatives of 6:hydroxy 2:methyl chroman (see structure below) where $R_1$, $R_2$ and $R_3$ may be hydrogen or methyl groups, that is, the α-5:7:8 tri-methyl; β-5:8 di-methyl; γ-7:8 di-methyl; and δ 8 methyl derivatives. In the tocopherols, $R_4$ is substituted by 4:8:12 tri-methyl tridecyl group and includes various stereoisomers and optical isomers (chiral centres are indicted by the *). In the tocotrienols, $R_4$ is substituted by 4:8:12 tri-methyl trideca-3:7:11 triene group and the 2 position may be stereoactive as R or S stereoisomers. Most preferably, the electron transfer agent is α-tocopherol.

The term "phosphate derivatives" is used herein to refer to compounds covalently bound by means of an oxygen to the phosphorus atom of a phosphate group thus forming a carbon-oxygen-phosphorous bond. The oxygen atom is typically derived from a hydroxyl group on the electron transfer agent. The term includes the acid forms of phosphorylated electron transfer agents, salts of the phosphates including metal salts such as sodium, magnesium, potassium and calcium and any other derivative where the phosphate proton is replaced by other substituents such as ethyl or methyl groups or phosphatidyl groups. The term includes mixtures of phosphate derivatives, especially those which result from phosphorylation reactions, as well as each of the phosphate derivatives alone. For example, the term includes a mixture of mono-tocopheryl phosphate (TP) and di-tocopheryl phosphate (T2P) as well as each of TP and T2P alone. Suitable mixtures are described in international patent application no PCT/AU01/01475.

The term "phosphate derivatives" does not include complexes of the phosphate derivatives with a complexing agent selected from the group consisting of amphoteric surfactants, cationic surfactants, amino acids having nitrogen functional groups and proteins rich in these amino acids.

Preferably, the one or more phosphate derivatives of one or more electron transfer agents is selected from the group consisting of mono-tocopheryl phosphate, di-tocopheryl phosphate and mixtures thereof. Most preferably, the one or more phosphate derivatives of one or more electron transfer agents is a mixture of mono-tocopheryl phosphate and di-tocopheryl phosphate.

In some situations, it may be necessary to use a phosphate derivative such as a phosphatide where additional properties such as increased water solubility are preferred. Phosphatidyl derivatives are amino alkyl derivatives of organic phosphates. These derivatives may be prepared from amines having a structure of $R_1R_2N(CH_2)_nOH$ wherein n is an integer between 1 and 6 and $R_1$ and $R_2$ may be either H or short alkyl chains with 3 or less carbons. $R_1$ and $R_2$ may be the same or different. The phosphatidyl derivatives are prepared by displacing the hydroxyl proton of the electron transfer agent with a phosphate entity that is then reacted with an amine, such as ethanolamine or N,N' dimethylethanolamine, to generate the phosphatidyl derivative of the electron transfer agent. One method of preparation of the phosphatidyl derivatives uses a basic solvent such as pyridine or triethylamine with phosphorous oxychloride to prepare the intermediate which is then reacted with the hydroxy group of the amine to produce the corresponding phosphatidyl derivative, such as P cholyl P tocopheryl dihydrogen phosphate.

The alkaloid formulation may be administered to humans or animals through a variety of dose forms such as supplements, enteral feeds, parenteral dose forms, suppositories, nasal delivery forms, dermal delivery including patches and creams, buccal delivery forms. Oral or buccal delivery may specifically suit alkaloids which have low water solubility. Preferably, oral alkaloid formulations according to the invention further comprise an enteric coating. The enteric coating protects the complexes from the acidic environment in the stomach. Oral formulations may take the form of tablets, powders, chewable tablets, capsules, oral suspensions, suspensions, emulsions or fluids, children's formulations, enteral feeds, nutraceuticals, and functional foods.

The dose form may further include any additives routinely used in preparation of that dose form such as starch or polymeric binders, sweeteners, coloring agents, emulsifiers, coatings and the like. Another suitable additive is a complex of a phosphate derivative of an electron transfer agents may also be utilized where additional properties such as improved stability or deliverability may be useful. The term "complexes of phosphate derivatives" refers to the reaction product of one or more phosphate derivatives of electron transfer agents with one or more complexing agents selected from the group consisting of amphoteric surfactants, cationic surfactants, amino acids having nitrogen functional groups and proteins rich in these amino acids as disclosed in international patent application no PCT/AU01/01476, incorporated herein by reference. If such an additive was used, it would be important to ensure that there was excess electron transfer agent present in the formulation. Other suitable additives will be readily apparent to those skilled in the art.

EXAMPLES

Various embodiments/aspects of the invention will now be described with reference to the following non-limiting examples.

Example 1

This example investigates the transdermal delivery to pigs of atropine in a formulation according to the invention. This experiment investigated the effects of dermal penetration of atropine when applied in gel form on heart rate of pigs.
Methods and Materials Atropine (20 mg/kg) was formulated in the following base creams for testing. In addition to the components specified below, all of the creams contained the following: 12% Ultrez-10 Carbomer-3% solution, 0.25% Triethanolamine, 0.1% Surcide DMDMH and Deionized Water up to 100%.

Compositions f, H and J when combined with atropine produce a formulation according to the invention. Compositions B, D and E produce formulations according to the prior art and compositions A, C and I illustrate the effect of the excipients.

| Code | Composition |
| --- | --- |
| A | 1.27% Deriphat 160 |
| B | 7.5% of 40% disodium lauryliminodipropionate monotocopheryl phosphate and lauryliminodipropionate ditocopheryl phosphate |
| C | 0.77% Arginine |
| D | 7.5% of 40% arginine monotocopheryl phosphate and arginine ditocopheryl phosphate |
| E | 7.5% of 40% arginine mono tocopheryl phosphate |
| F | 3% mono tocopheryl phosphate |
| G | 3% mono tocopheryl phosphate and ditocopheryl phosphate |
| H | 7.5% disodium lauryliminodipropionate mono tocopheryl phosphate |
| I | 1.5% Triethanolamine |
| J | Tocopheryl phosphate and di-tocopheryl phosphate |

Ten male crossbred (Large white×Landrace) pigs (initial average weight 51.5 kg and final average weight of 61.0 kg) were utilised in this experiment. Four days prior to the study fourteen pigs were weighed and randomly allocated to individual pens (1.75 m×0.65 m) in the experimental facility for an acclimatisation period. During this period the hair on the back of the pigs was removed with animal clippers (Oster—U.S.A) followed by regular shaving with an electric human shaver (Philishave HQ5041—Philips Aust Pty Ltd). Elastic belts were also placed around the chest of the pigs to accustom them to wearing the heart rate monitors. At the start of the experiment the ten pigs that adapted best to the environment and regular handling were selected and housed such that there were no pigs in adjacent pens. This physical separation of the pigs avoided any potential conflict between signals from the heart rate monitors which all operated at the same frequency. The ten pigs were divided into two groups of five (odd and even numbers) and utilised on alternate days in the experiment. An experimental replicate was therefore performed over two consecutive treatment days. Within each replicate the ten pigs were randomly assigned to one of the ten treatment groups, therefore each pig was used for data capture on five occasions, and each treatment was applied five times.

On each measurement day by about 08:00 the five pigs under experiment were weighed, fitted with heart rate monitors and recording of heart rate at 1-minute intervals commenced. Human heart rate monitors (Polar Sport Tester PE4000—Polar Electro Finland) were used to capture heart rate data. Chest belts with in-built sensors and transmitters were fitted around the pig's chest just behind the front legs. These belts had a liberal coating of an ultra-sonic gel (Virbac Aust Pty Ltd) applied to the sensor contact areas to ensure a good heart rate signal was obtained. A second belt fabricated from 100 mm wide elastic and velcro was placed around the pigs over the transmitter belt. This belt protected the transmitter from physical damage and included a pocket for storage of the monitor recording unit (similar to a wristwatch) during the recording period. An area on the back of the pigs was then shaved with the electric human shaver. Within this shaved area a template and permanent marker was used to outline a rectangular treatment application area of 172.5 cm$^2$ (75×230 mm). Feed was then offered at 100 g/kg liveweight$^{0.75}$ (eg: 55 kg pig=2020 g/d). Treatment application was begun at least 1 h after the commencement of heart rate recording. Three staff wearing protective rubber gloves applied each of the test formulations in 5 ml syringes. This involved rubbing the products into the skin of the pig while an assistant directed warm air from an electric hair dryer onto the treatment area. Rubbing was discontinued after approximately 8 to 10 minutes when the skin surface became tacky to touch. Three (10×12 cm) transparent dressings (Tegaderm—3M Health Care U.S.A.) were then applied over the treatment area. Following treatment application the pigs were left undisturbed for the remaining 6 to 7 hours of the recording period. Syringes and gloves used in treatment applications were weighed before and after application to enable accurate calculation of the actual doses applied to the pigs. At the conclusion of the recording period, the heart rate monitors and the transparent dressings were removed and the treatment application area was washed down with warm water containing a small quantity of a liquid handwash.

Results

TABLE 1

Effect of various atropine preparations on average heart rate over 60 minute intervals.

| | A | B | C | D | E | F | G | H | I | J | sed | $\chi^2$ |
|---|---|---|---|---|---|---|---|---|---|---|---|---|
| Heart rate (bpm) | | | | | | | | | | | | |
| −60-0 min | 148 | 147 | 148 | 154 | 148 | 152 | 151 | 149 | 150 | 146 | 5.52 | 0.916 |
| 0-60 min | 173 | 155 | 176 | 155 | 165 | 162 | 180 | 170 | 155 | 154 | 9.33 | 0.007 |
| 60-120 min | 186 | 170 | 184 | 169 | 170 | 175 | 196 | 190 | 164 | 165 | 10.91 | 0.011 |
| 120-180 min | 161 | 156 | 162 | 154 | 148 | 165 | 168 | 171 | 144 | 153 | 10.46 | 0.124 |
| 180-240 min | 145 | 148 | 146 | 149 | 139 | 156 | 152 | 164 | 144 | 149 | 9.87 | 0.353 |
| 240-300 min | 144 | 146 | 150 | 142 | 147 | 147 | 146 | 155 | 139 | 136 | 7.93 | 0.471 |
| 300-360 min | 143 | 142 | 144 | 131 | 137 | 142 | 147 | 150 | 135 | 136 | 7.60 | 0.271 |
| Difference from baseline (bpm) | | | | | | | | | | | | |
| 0-60 min | 24.2 | 8.7 | 28.5 | 1.1 | 16.1 | 10.3 | 30.7 | 20.0 | 4.9 | 7.1 | 10.41 | 0.021 |
| 60-120 min | 37.8 | 22.8 | 35.6 | 14.1 | 21.7 | 22.6 | 46.8 | 40.9 | 13.2 | 19.0 | 12.58 | 0.045 |
| 120-180 min | 13.0 | 8.9 | 13.2 | −1.4 | −0.8 | 12.8 | 20.1 | 21.2 | −6.8 | 8.0 | 11.71 | 0.196 |

TABLE 2

Effect of various atropine preparations on average heart rate over 60 minute intervals.

| | A | B | C | D | E | F |
|---|---|---|---|---|---|---|
| Log peak rate (bpm) | 2.341 (219) | 2.307 (203) | 2.33 (214) | 2.29 (195) | 2.313 (206) | 2.326 (212) |
| Log time to peak (min) | 1.790 (61.7) | 1.904 (80.2) | 1.762 (57.8) | 1.872 (74.5) | 1.726 (53.2) | 1.787 (61.2) |
| Log ascending slope[1] | 0.125 (1.33) | 0.003 (1.01) | 0.171 (1.48) | −0.060 (0.87) | 0.061 (1.15) | 0.229 (1.69) |
| Log descending slope[1,2] | −0.244 (0.57) | −0.312 (0.49) | −0.206 (0.62) | −0.124 (0.75) | −0.186 (0.65) | −0.393 (0.40) |
| Log ratio of slopes[2] | 0.354 (2.26) | 0.292 (1.96) | 0.393 (2.47) | 0.072 (1.18) | 0.264 (1.84) | 0.624 (4.21) |

| | G | H | I | J | sed | $\chi^2$ |
|---|---|---|---|---|---|---|
| Log peak rate (bpm) | 2.351 (224) | 2.321 (209) | 2.301 (200) | 2.288 (194) | 0.0233 | 0.078 |
| Log time to peak (min) | 1.738 (54.7) | 1.734 (54.2) | 1.764 (58.1) | 1.786 (61.1) | 0.0953 | 0.452 |

TABLE 2-continued

Effect of various atropine preparations on average heart rate over 60 minute intervals.

| | | | | | | |
|---|---|---|---|---|---|---|
| Log ascending slope[1] | 0.434 (2.72) | 0.250 (1.78) | 0.211 (1.62) | 0.117 (1.31) | 0.1568 | <0.001 |
| Log descending slope[1,2] | −0.375 (0.42) | −0.427 (0.37) | −0.299 (0.50) | −0.049 (0.89) | 0.1095 | <0.001 |
| Log ratio of slopes[2] | 0.808 (6.43) | 0.680 (4.79) | 0.495 (3.13) | 0.196 (1.57) | 0.2052 | <0.001 |

[1]units are bpm per min
[2]units should be negative but were multiplied by −1 so that a log transformation could be performed.

TABLE 3

Effect of various base cream preparations on average heart rate over 60 minute intervals.

| | A | B | C | D | E | F | G | H | I | J | sed | $\chi^2$ |
|---|---|---|---|---|---|---|---|---|---|---|---|---|
| Heart rate (bpm) | | | | | | | | | | | | |
| −60-0 min | 146 | 147 | 147 | 143 | 145 | 127 | 145 | 135 | 124 | 132 | 11.1 | 0.283 |
| 0-60 min | 139 | 140 | 129 | 144 | 138 | 123 | 142 | 120 | 123 | 128 | 10.7 | 0.141 |
| 60-120 min | 125 | 132 | 124 | 137 | 134 | 122 | 139 | 120 | 120 | 132 | 10.9 | 0.587 |
| 120-180 min | 128 | 126 | 126 | 131 | 135 | 119 | 130 | 125 | 119 | 124 | 6.7 | <0.001 |
| 180-240 min | 125 | 121 | 132 | 134 | 129 | 121 | 132 | 122 | 114 | 122 | 8.7 | 0.358 |
| 240-300 min | 137 | 122 | 130 | 132 | 120 | 112 | 139 | 130 | 121 | 122 | 9.0 | 0.040 |
| 300-360 min | 131 | 120 | 132 | 127 | 116 | 110 | 134 | 126 | 110 | 125 | 6.0 | <0.001 |
| Difference from baseline (bpm) | | | | | | | | | | | | |
| 0-60 min | −4.4 | −5.1 | −16.5 | 1.4 | −6.6 | −6.3 | −2.7 | −12.5 | −0.9 | −5.8 | 6.16 | 0.162 |
| 60-120 min | −16.7 | −15.3 | −20.1 | −3.8 | −10.3 | −7.0 | −6.5 | −13.7 | −5.5 | −4.4 | 11.44 | 0.708 |
| 120-180 min | −15.0 | −16.0 | −21.1 | −9.9 | −9.8 | −9.8 | −15.8 | −8.3 | −4.1 | −8.6 | 12.62 | 0.971 |

Discussion and Conclusion

The data suggests that transdermal application of atropine will increase heart rate in the pig with the peak occurring approximately 60 minutes after application. The data also suggests that the base creams alone do not increase heart rate and that the affects of the preparations are due to the atropine itself.

Formulation G which contains the tocopheryl phosphate/di-tocopheryl phosphate mixture provided the best delivery system for atropine. The heart rate increased and remained sustained for longer periods compared to the other formulations. This is shown in table 1, where under the heading "Differences from baseline" the values at the 0-60 min and 60-120 min are greatest with G. Table 1 demonstrates that Formulation G is consistently more effective than a similar concentration of atropine in compositions containing the lauryliminodipropionate-tocopheryl phosphates.

The evaluation of the data in Table 2 shows that there is a consistent increased efficacy of formulation G versus formulation H for log peak rate, log time to peak and, importantly, log ascending slope and log descending slope.

Further, the formulation according to the invention caused no inflammation, thus it appears possible to allow prolonged dermal contact without causing irritation.

Example 2

This example investigated the effect of transdermal delivery to pigs of morphine. The skin of pigs has similar properties to human skin and as such the pig is an excellent model for studying dermal delivery of drugs.

This study was designed to assess the level of analgesia as measured by a delay in the tail flinch response to a heat (62° C.) placed on the rump following the transdermal delivery to pigs of morphine.

Flinch test data were analysed by REML (Residual maximum likelihood) with treatment and time as the fixed model and pig, replicate and flinch time at time zero as the random model. Data were initially analysed raw but because there were some skewed data at 6 h they were also log-transformed for analyses. Either analyses provided essentially the same interpretation.

The following formulations were tested:

| Code | Composition |
|---|---|
| AGM | Morphine in formulation G as per Example 1. |
| AG | Formulation G with no morphine |
| AHM | Morphine in formulation H as per Example 1. |
| AH | Formulation H with no morphine. |

Figure 1:
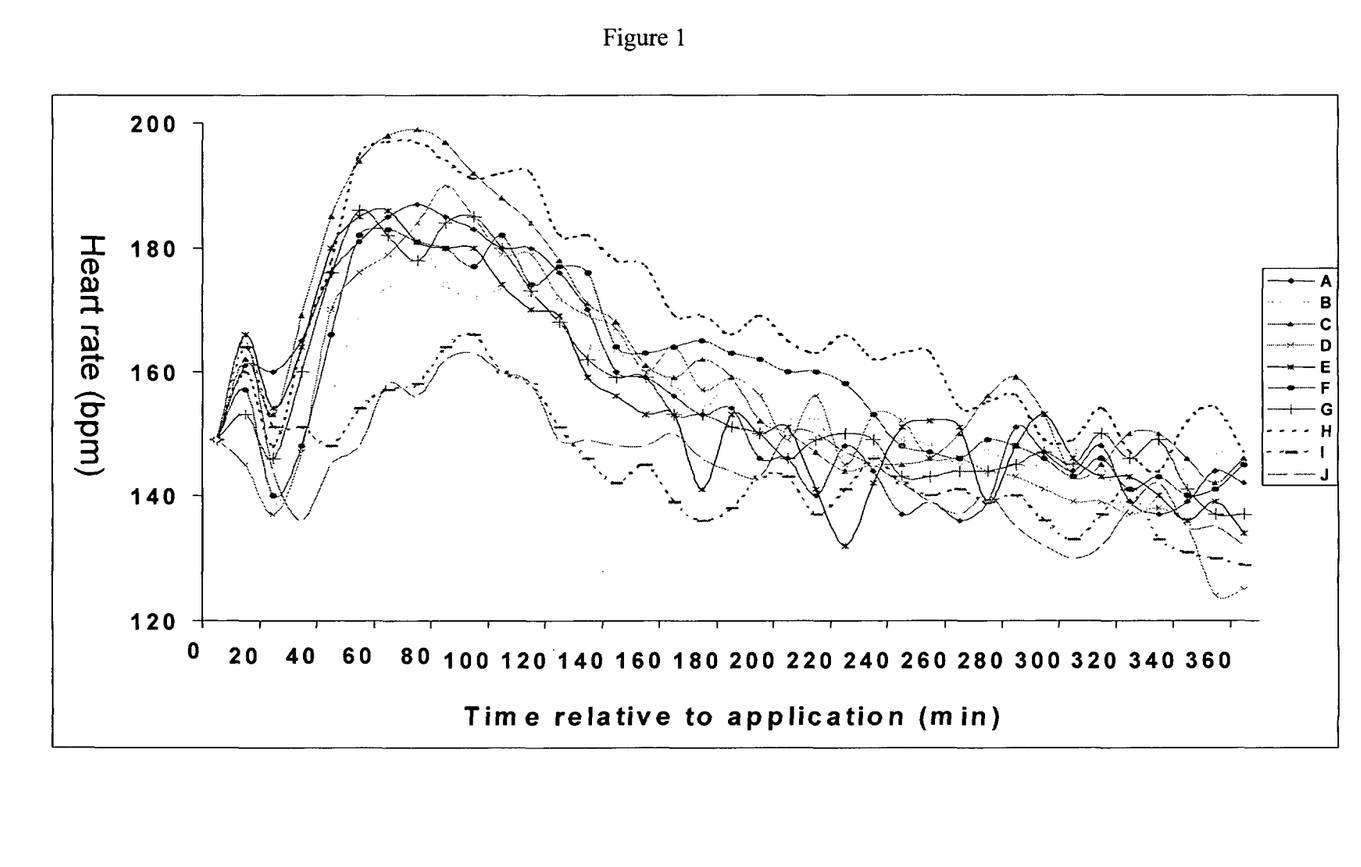
FIG. 1: Effect of various atropine formulations on heart rate in pigs. Data are cumulative averages over 10 minute periods and have been corrected for basal (average of 1 h before application) using covariate analyses.
Figure 2:
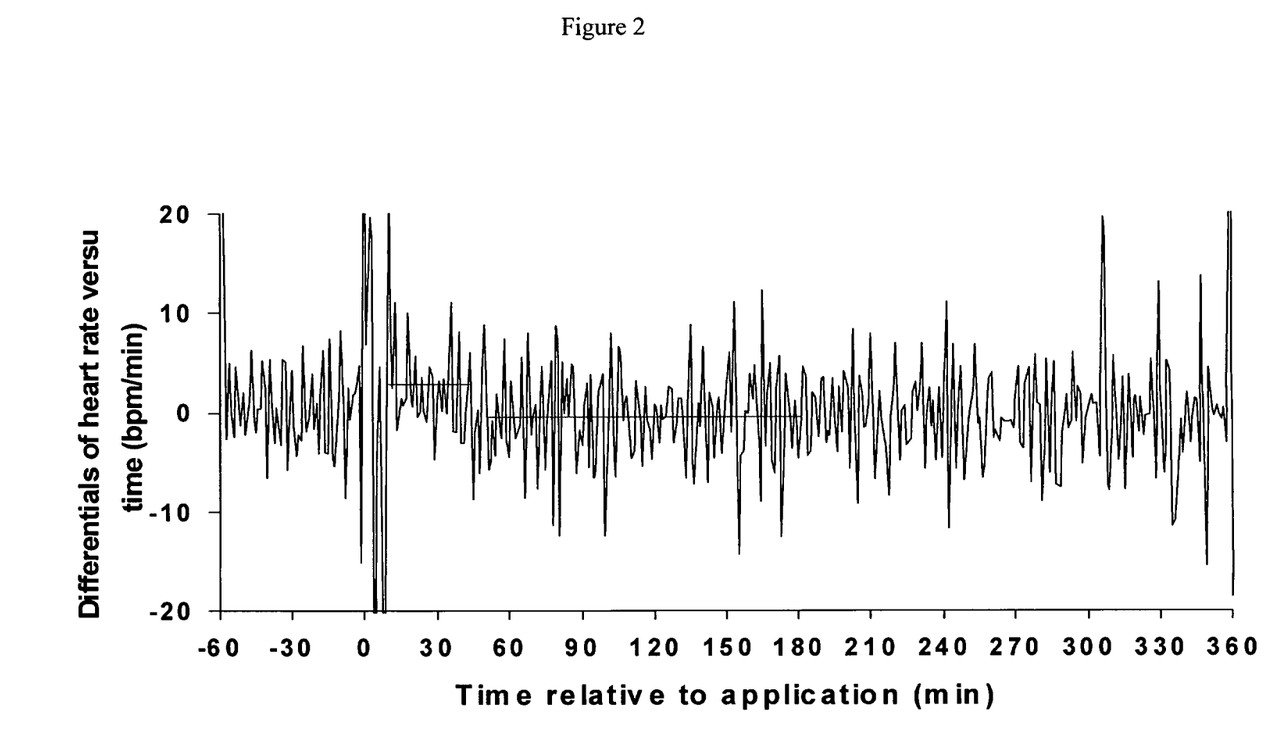
FIG. 2: Typical differential of heart rate versus time curve. Data are from pig 1 during replicate 1 who was treated with preparation C (ie the very first pig used). The treatment application commenced at 0 minutes and continued for 6 minutes. The period over which differentials were averaged is indicated by the straight lines.
Figure 3:
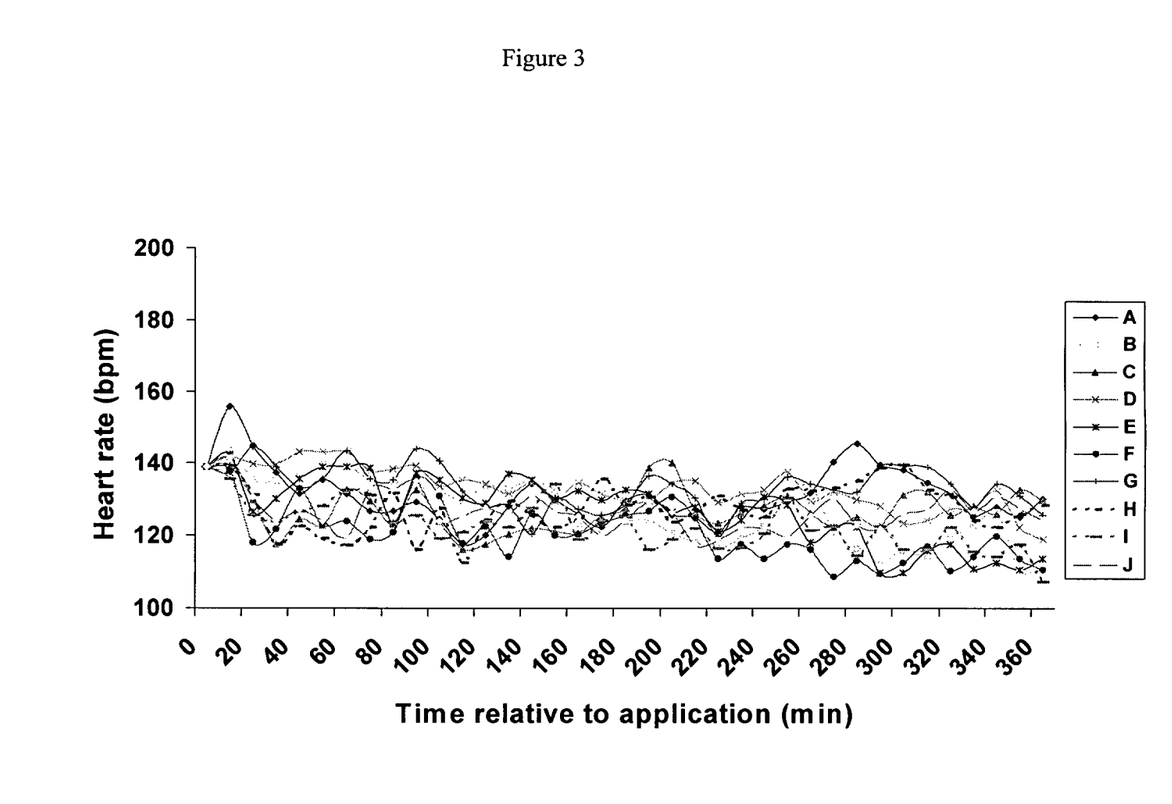
FIG. 3: Effect of various base creams on heart rate in pigs. Data are cumulative averages over 10 minutes periods and have been corrected for basal (average of 1 h before application) using covariate analyses.
Figure 4:
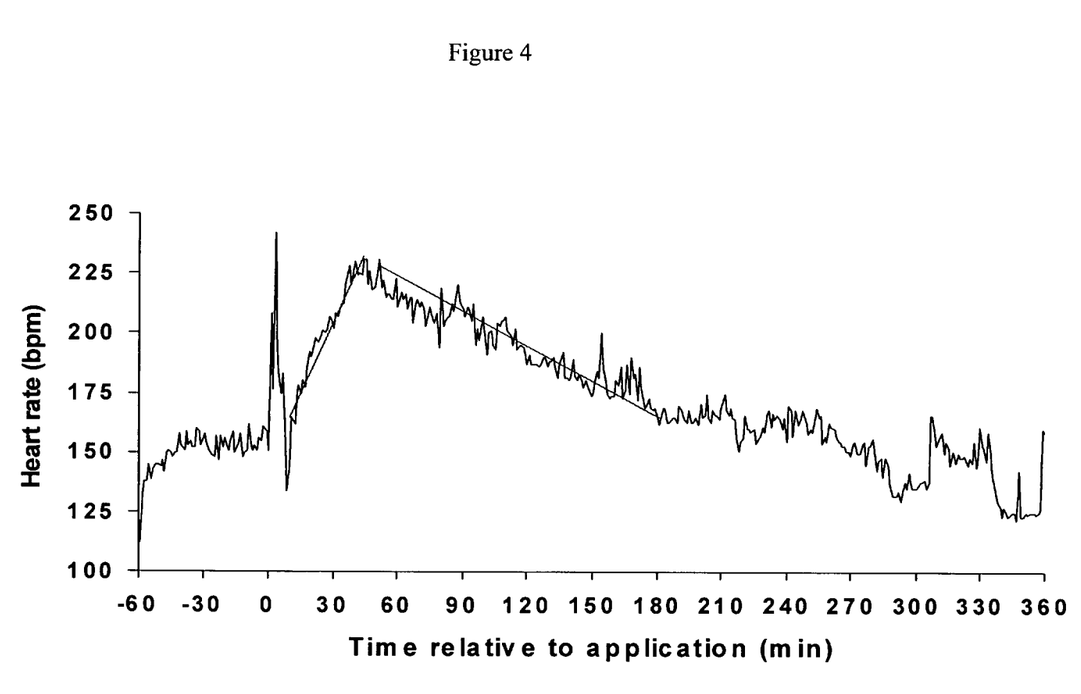
FIG. 4: Typical heart rate versus time curve. Data are from pig 1 during replicate 1 who was treated with preparation C (ie the very pig used). The treatment application commenced at 0 minutes and continued for 6 minutes. The period over which differentials were averaged is indicated by the straight lines.
Figure 5:
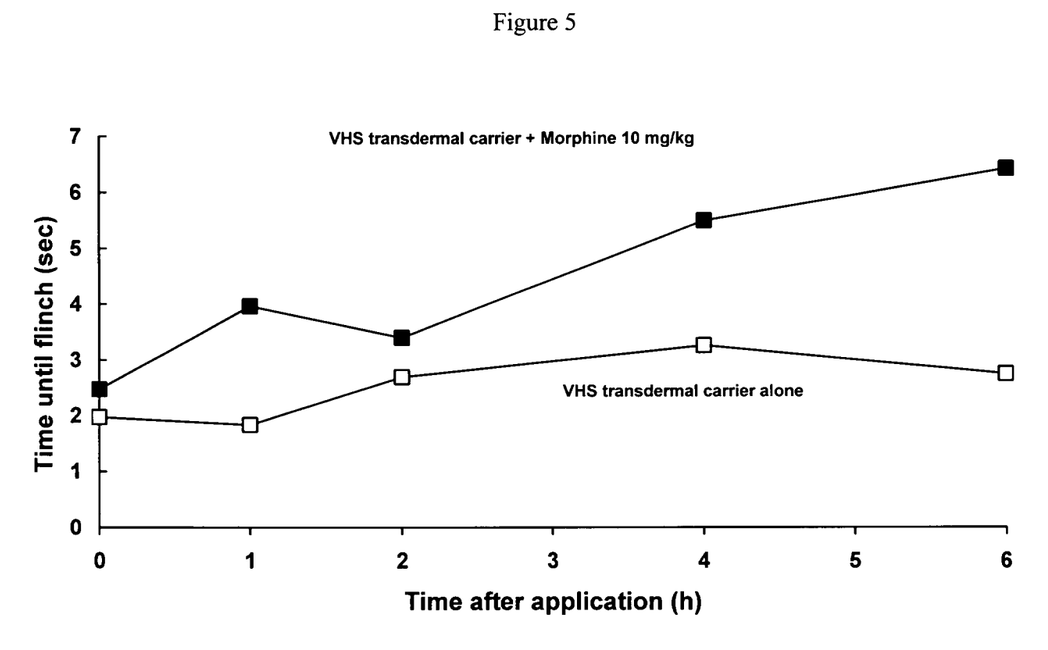
FIG. 5: Effect of treatment and time flinch response after heat probe application

Overall, the flinch time for pigs treated with preparation AGM had a greater flinch time than any of the other treatments (2.63, 2.88, 4.82 and 3.17 seconds for treatments AG, AH, AGM and AHM, Table 4). Interestingly, the response was greatest at 6 h after treatment (FIG. 5) suggesting a sustained effect, particularly when compared to the control AG. In this context the flinch test was 133% greater at 6 h in pigs treated with AGM compared to AG. There was an indication that AHM had a greater flinch time at 2 h after treatment when compared to the control AH, but this was not sustained. AHM did not provide the sustained results which were obtained with AGM.

In conclusion, the data demonstrates that transdermal delivery of morphine in a formulation according to the invention (AGM) provides rapid and sustained analgesia as measured by a delay in the tail flinch response to a heat treatment at 1 to 6 h. Further, the formulation according to the invention caused no inflammation, thus it appears possible to allow prolonged dermal contact without causing irritation.

used in this experiment and is listed here as a comparison of the components between Vital ET and the formulation of the invention.

TABLE 4

Effect of treatment and time flinch response after heat probe application (seconds)[1]

| | Time after treatment (h) | | | | | Significance ($\chi^2$) | | |
|---|---|---|---|---|---|---|---|---|
| | 1 | 2 | 4 | 6 | sed[1] | Treat | Time | Tr × Ti |
| AG | 1.83 | 2.69 | 3.26 | 2.75 | 1.087 | <0.001 | 0.062 | 0.45 |
| AH | 2.10 | 2.34 | 3.60 | 3.50 | | | | |
| AGM | 3.96 | 3.40 | 5.49 | 6.42 | | | | |
| AHM | 2.85 | 3.87 | 2.97 | 3.00 | | | | |
| AG | (0.260) | (0.411) | (0.461) | (0.413) | 0.0858 | 0.003 | 0.011 | 0.85 |
| AH | (0.313) | (0.335) | (0.465) | (0.438) | | | | |
| AGM | (0.460) | (0.470) | (0.570) | (0.622) | | | | |
| AHM | (0.410) | (0.466) | (0.440) | (0.458) | | | | |

[1]Values in parentheses are log transformed.
[2]standard error of the difference for time × treatment. For treatment and time effects multiply by 0.511 and 0.497, respectively.

Example 3

This example investigates the effect of different formulations according to invention when compared to a control using complexed tocopheryl phosphate on transdermal delivery of morphine to rats.

Methods

Animals: Conscious Sprague Dawley Rats (~280 g) n=6 per group.

Transdermal Formulation Preparation: Morphine HCl, Glaxo Australia Pty Ltd (catalogue number 22284). Morphine free base was derived from HCL form in aqueous solution by the addition of potassium carbonate. This process was completed at Monash University. (Morphine HCl could not be used with creams, so free base was used).

Morphine (10 mg/kg) was applied in each of the formulations set out in Table 5. The effect was measured by the delayed response of the rat to heat with the delay in time taken to withdraw the pat taken as the action of morphine.

Test Method:

The plantar analgesiometer is designed for rapid and efficient screening of analgesia levels in small laboratory animals. The device is used to apply a heat source (~45° C. from an infrared light) to the animal's hind paw and the time taken to withdraw the paw is measured (paw withdrawal latency). The hot plate provides a constant surface temperature, with a built-in digital thermometer with an accuracy of 0.1° C. and a timer with an accuracy of 0.1 second. The animal is placed on a hot plate, confined by a clear acrylic cage which surrounds the plate and paw-lick response is monitored. An increased time period before paw-lick response indicating analgesia.

Rats had a hair removal cream applied to a dorsal hindquarter area of skin (under anaesthesia) at least 24 hours prior to any transdermal patch application. Conscious Sprague Dawley rats (~400 grams) received morphine at a dose of 10 mg morphine HCl per kg body weight. The formulation contained 10% w/w morphine.HCl, and for a 0.2 kg rat the amount applied was 20 mg of formulation that contained 2 mg

TABLE 5

Formulations of tocopheryl phosphates

| Ingredient | Purpose | Vital-ET ™ | TP/T$_2$P | TPM-01 | TPM-01/M |
|---|---|---|---|---|---|
| Disodium tocopheryl phosphate | Transdermal agents | 2.00% | 2.00% | 2.00% | 7.20% |
| Di-tocopheryl phosphate | | 1.00% | 1.00% | 1.00% | 3.60% |
| Lauryldiaminopropionic acid | Complexing agent | 3.00% | — | — | — |
| Morphine HCl USP-NF | Active Ingredient | — | — | — | 5.4% |
| Ultrez-10 carbomer-3% solution | Excipient | 0.36% | 0.36% | — | — |
| Carbomer 934 USP-NF | | — | — | 0.36% | 0.36% |
| Triethanolamine (trolamine) USP | Excipient | 0.25% | 0.25% | 0.25% | 0.25% |
| Surcide DMDMH | preservative | 0.10% | 0.10% | — | — |
| Germall 115 | preservative | — | — | — | — |
| Methylparaben USP-NF, BP | preservative | 0.10% | — | 0.10% | 0.10% |
| Purified water USP-NF | Solvent | QS 100% | QS 100% | QS 100% | QS 100% |

The base gels used as controls contained all of the ingredients except for the tocopheryl phosphate. Vital ET was not morphine.HCl. A single application was used in the morning, with measures of the analgesia made at various time-points.

The skin area exposed to drug/vehicle was then covered with a Tegaderm patch. All animals underwent analgesic testing before and after morphine administration.

Figure 6:
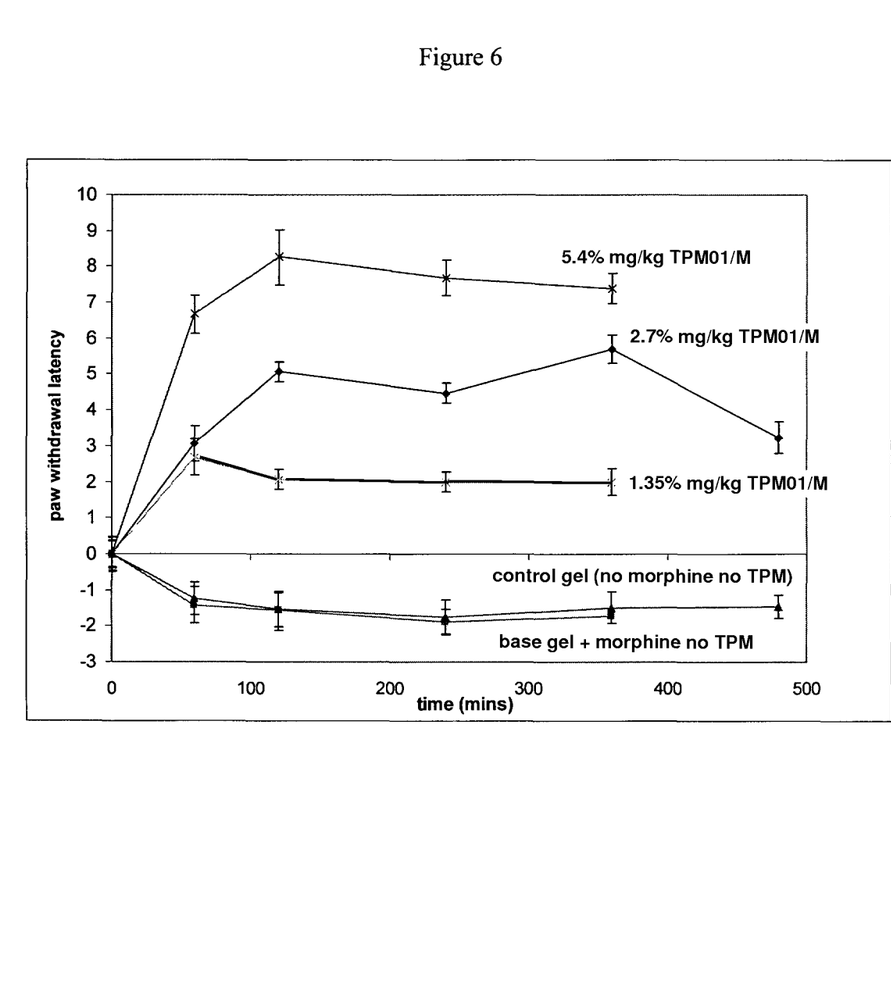
FIG. 6: Effect of morphine 1.35, 2.7 and 5.4 mg/kg in TPM-01/M formulation on paw withdrawal latency, tested up to 8 hours.

Results:

FIG. 6 illustrates the results achieved with each of the formulations. The results show an increase in response time, indicating analgesia, in a dose-dependant manner. The control test of gel with morphine but no TPM show the essential requirement of TPM for the transdermal route to work. Results are expressed as change in withdrawal time compared to controls, where control values are from rats treated with incomplete formulations (i.e., no morphine or no TPM), as well as the zero-time values for rats treated with complete the formulation, TPM-01/M)

Conclusion:

The formulation used in this study contains TP/T2P mix (or TPM), morphine.HCl and other excipients as listed in table 5. The formulation did not contain any lauryldiaminoproprionic acid.

FIG. 6 shows a clear dose-response and a sustained affect. When compared to the 2 types of control (ie, a control gel with base excipients only, and no morphine and no TP/T2P mix, and a control gel with base excipients and morphine but no TP/T2P) the results show that morphine is best delivered when formulated with the TP/T2P mix.

The word 'comprising' and forms of the word 'comprising' as used in this description and in the claims does not limit the invention claimed to exclude any variants or additions. Modifications and improvements to the invention will be readily apparent to those skilled in the art. Such modifications and improvements are intended to be within the scope of this invention.

What is claimed is:

1. A composition comprising a complex 1) of an alkaloid comprising a tertiary amine, and a 2) a mixture of a mono-tocopheryl phosphate and a di-tocopheryl phosphate.

2. The composition of claim 1, wherein the alkaloid comprises an alicyclic tertiary amine wherein the nitrogen atom is a common member of three rings, a cyclic tertiary amine wherein the nitrogen is incorporated into a single ring and alkylated, or a non-cyclic tertiary amine wherein the nitrogen is not incorporated into a ring.

3. The composition of claim 1, wherein the alkaloid comprises an opioid.

4. The composition of claim 1, wherein the alkaloid comprises at least one of atropine, quinine, fentanyl, nicotine, fenspiride, flurazepam, morphine, codeine, or a mixture thereof.

5. The composition of claim 4, wherein the alkaloid comprises atropine.

6. The composition of claim 4, wherein the alkaloid comprises morphine.

7. A pharmaceutical formulation comprising the composition of claim 1 and a carrier.

8. A topical formulation comprising the composition of claim 1.

9. An oral formulation comprising the composition of claim 1.

10. The oral formulation of claim 9, further comprising an enteric coating.

11. The oral formulation of claim 9, wherein the formulation is a tablet, a powder, a chewable tablet, a capsule, an oral suspension, a suspension, an emulsion, a children's formulation, an enteral feed, a nutraceutical, or a functional food.

12. A buccal formulation comprising the composition of claim 1.

* * * * *